United States Patent [19]

Crafton

[11] 4,383,377
[45] May 17, 1983

[54] HOT AIR DRYER ROOM DEODORIZER

[76] Inventor: Thomas W. Crafton, 7661 Charlotte Ave., Nashville, Tenn. 37209

[21] Appl. No.: 208,188

[22] Filed: Nov. 19, 1980

[51] Int. Cl.³ .............................................. F26B 21/14
[52] U.S. Cl. .......................................... 34/60; 34/90; 34/202; 239/60; 239/136; 422/124
[58] Field of Search ...................... 422/124, 125, 305; 239/57, 60, 129, 136; 219/276, 373; 34/60, 90, 91, 202, 243 R

[56] References Cited

U.S. PATENT DOCUMENTS

| | | | |
|---|---|---|---|
| 1,646,365 | 10/1927 | Willis | 219/276 |
| 2,281,370 | 4/1942 | Morrison et al. | 34/91 |
| 2,890,761 | 6/1959 | Davidson | 239/57 |
| 3,192,008 | 6/1965 | Dwyer | 422/124 |
| 3,442,197 | 5/1969 | Cobarg | 422/305 |
| 3,990,848 | 11/1976 | Corris | 422/124 |
| 4,195,416 | 4/1980 | Hall | 34/90 |

FOREIGN PATENT DOCUMENTS 2394298  2/1979  France ............................ 422/124

Primary Examiner—Larry I. Schwartz
Attorney, Agent, or Firm—Pitts, Ruderman & Kesterson

[57] ABSTRACT

Apparatus for efficiently and inexpensively deodorizing rooms, such as restrooms in commercial establishments, on an as needed basis is disclosed. The apparatus operates in conjunction with a standard hot air hand dryer commonly found in public and commercial washrooms, restrooms, showers, and the like. When the hot air dryer is used in conjunction with this invention, a powerful flow of air is moved past a deodorizer source thereby providing the deodorizing. Thus, the more useage of the hot air dryer, the more room deodorizing is provided. The apparatus includes a cup or housing container which is securely mounted or attached to the intake grill of the hot air hand dryer. The cup or container includes openings or apertures at selected locations such that the free flow of intake air is not inhibited. There is also included, in an unobvious location of the cup, a larger opening or slot suitable for placing a stick or disk of a vaporizable deodorizer in the container. Thus, in operation, the cold air is drawn through the apertures of the cup or container pass the deodorizing source on and into the hot air dryer itself. This cold air with the vaporizable deodorizer suspended therewith is then heated and used in the normal way for hot air drying. Thus, it will be appreciated that the deodorized air is exhausted as hot deodorized air from the hot air dryer.

2 Claims, 10 Drawing Figures

U.S. Patent   May 17, 1983   4,383,377
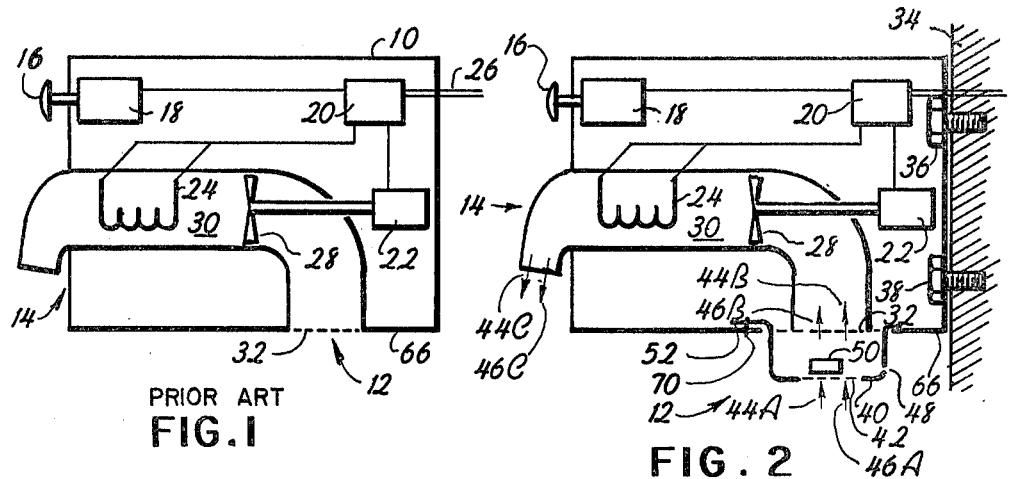
PRIOR ART
FIG. 1
FIG. 2
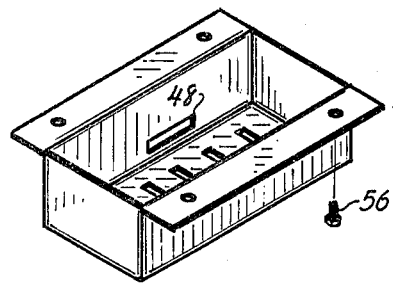
FIG. 3
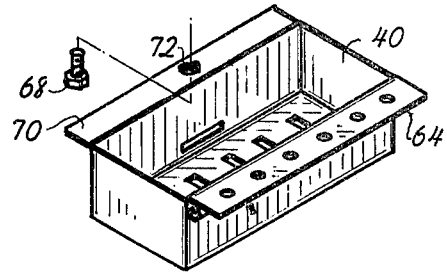
FIG. 7
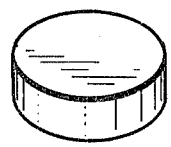
FIG. 4A
FIG. 6
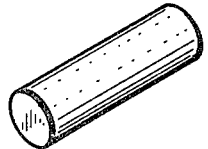
FIG. 4B
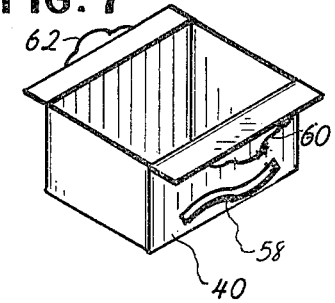
FIG. 5
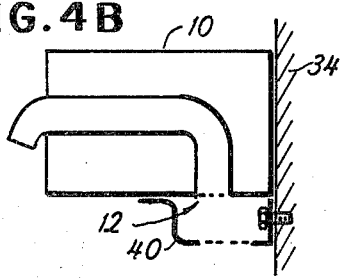
FIG. 8
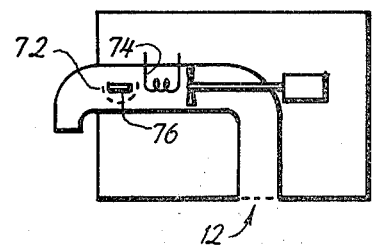
FIG. 9

HOT AIR DRYER ROOM DEODORIZER

BACKGROUND OF THE INVENTION

This invention relates to simple and inexpensive deodorizing equipment, and is particularly useful in commercial and public washrooms, restrooms, showers, and the like where the deodorizing of such public facilities becomes a severe problem. The apparatus of this invention simply attaches to the existing hot air hand dryers without installation costs or further expense. Although bathroom or washroom deodorizing is not a particular problem in the private home, it does become a significant problem with respect to public or commercial washrooms because of the large traffic and usage. Consequently, it is a common practice in most public and commercial restrooms and washrooms to provide some sort of deodorizing system. The most commonly used type of deodorizing systems are deodorizing sources manufactured in a vaporizable gel form so that when they are exposed to the air they evaporate or sublime, and the deodorizing vapor is distributed throughout the air. These gel type deodorizers are typically simply laid in the bottom of a public urinal or hung over the side of a toilet. In addition, there are deodorizing systems which include means to increase the air flow pass the gel product to increase the vaporization process. To this end, refer to U.S. Pat. No. 3,990,848 issued to Charles James Corris on Nov. 9, 1976. According to this patent, there is disclosed a system which induces air flow pass the gel type deodorizer and into the environment. The system uses a cartridge or gel source supported by a pourous container along with an energy such as a battery. A small fan suitable for being driven by the battery is contained in a housing such that an air flow is created up through the pourous container pass the vaporizable deodorizing gel, pass the fan and out a top grating. Thus, an air flow is created such that the vaporizable deodorant is dispersed throughout the room. The deodorizing system such as that described in the Corris patent, also typically includes a timing source such that the fan is operated only for a short period of time at regular intervals. Unfortunately, this type of room deodorizer may be operating in the middle of the night when there is no use of the restroom or washroom and may be off during periods of maximum traffic through the washroom. Furthermore, the use of batteries to drive such systems becomes quite an expense over a period of time. Finally, such systems are usually somewhat fragile and those mounted to the wall of a public restroom are commonly destroyed or vandalized. However, it will be appreciated that even without the cost of the battery, or the exposure to vandalism and the like, the room deodorizer simply will not always operate when it is needed.

To this end, referring now to U.S. Pat. No. 3,192,008 by M. J. Dryer there is shown a room deodorizer which does operates on somewhat of an as needed basis. According to this patent, a fan and deodorizing unit is attached to the side of a standard or paper cloth hand towel dispenser. Rotation of the roll of toweling winds a spring which in turn activates an impellar. The container on the side of the hand towel dispenser also includes a vaporizable deodorant material such that air flow is drawn pass the deodorizing material by the small impellar and out the exhaust port at the top. Thus, it will be appreciated that the more the hand towel dispenser is used the more deodorizer provided. However, it will also be appreciated that the impellar gearing mechanism and springs and other mechanical devices necessary to operate this system will be expensive; and further, the small amount of air flow created in such a manner simply cannot be completely effective for deodorizing a large public restroom or washroom.

In many public restrooms and washrooms today, it is becoming more and more common to find hot air hand dryers. These dryers expell a significant volume of air and have electrical heating elements which heat the air to a high temperature before directing it out of an exhaust port for purposes of drying a persons hands or face. The use of these hot air dryers is becoming more and more prevalent as they require less maintenance and attention than towels. Furthermore, they create no disposal problems. It is anticipated, that in the future such hot air dryers will substantially replace the paper and cloth hand towels now provided in most public and commercial restrooms and washrooms. Although the most common hot air hand dryers simply includes a motor which drives a large squirrel cage blower to move a large portion of air, it will be appreciated that any type of air source may be used such as a compressed air source described in U.S. Pat. No. 2,859,535 issued to J. W. Carlson on Nov. 11, 1958.

SUMMARY

Therefore, it is an object of this invention to provide an effective room deodorizer which operates on an as needed basis.

It is a further object of this invention to provide a room deodorizer which is simple and inexpensive to maintain and operate.

It is yet another object of this invention to provide a room deodorizer which requires no additional energy sources.

It is also an object of this invention to provide a room deodorizer which is substantially immune to vandalism and damage.

To accomplish the mentioned objects as well as other objects which will become evident from the drawings and detailed description, the present invention provides apparatus in combination with a hot air hand dryer having a housing which includes an air intake port and an air exhaust port. The hand dryer also includes an air moving drive such as a fan or squirrel cage blower which is typically driven by an electrical motor. Such an air moving device draws air into the housing through the intake port and exhausts the air from the housing through the exhaust port. A heater such as electrical heating coils, for example, are included within the housing and in the path of the air flow through the housing. These heating coils heat the air as it flows therethrough. This invention also includes a switch for providing and/or interrupting electrical energy to the motor and the heating means. The room deodorizer improvement to this hot air hand dryer includes a container or cup means positioned proximate the intake port of the dryer. In a preferred embodiment, the container is simply a perforated cup which snaps in place at the grating located at the intake port. The perforations of the container are sufficient to allow the air flow therethrough and also include a larger opening for purposes of inserting a vaporizable deodorizing source such as gel in the container. Thus, when the hot air hand dryer is activated, a significant quantity or volume of room air is drawn through the perforations of the container, pass the vaporizable deodorant and on into the hot air dryer. The deodorized air is then heated and exhausted at the exhaust port.

In an alternate embodiment, a container containing the vaporizable deodorant may be included within the housing downstream of the heating element and prior to the exhaust port. However in such an embodiment, it will be necessary to use a deodorant source which has a much higher vaporizing temperature. It will be appreciated that the use of a deodorizing source having a higher vaporizable temperature will not vaporize in free air as quickly as one having a lower vaporizable temperature. Thus, in such an embodiment the room deodorizing will take place only when the dryer is activated.

BRIEF DESCRIPTION OF THE DRAWINGS

FIG. 1 shows a diagrammatical schematic of a prior art hot air dryer.

FIG. 2 shows the hot air hand dryer of FIG. 1 including the improvement deodorizing feature of this invention.

FIG. 3 illustrates a typical container for holding a quantity of vaporizable deodorant material.

FIGS. 4A and 4B show sample shapes of a vaporizable deodorant gel source which may be used with the container of FIG. 3.

FIG. 5 shows an alternate design of a container for attaching to a hot air dryer which includes a serpentine opening for receiving the vaporizable material while inhibiting the introduction of foreign materials.

FIG. 6 shows a serpentine shaped vaporizable deodorant source for use with container of FIG. 5.

FIG. 7 shows an alternate technique for attaching the container used in this invention to the hot air dryer.

FIG. 8 shows the container of this invention attached in closed proximity to the standard hot air dryer.

FIG. 9 shows an alternate embodiment of the present invention.

DESCRIPTION OF THE INVENTION

Referring now to FIG. 1, there is shown a diagrammatic illustration of the prior art hot air hand dryer. As seen in FIG. 1, there is shown a housing 10 having an inlet port 12 and an exhaust port 14. Also shown, is a pushbutton unit 16 for activating a timer switch 18 in turn controls switch unit 20 such that power may be supplied to drive motor 22 and heating element 24 from an outside power source 26 such as standard 110 v AC power. Motor 22 in turn drives a fan, impellar, squirrel cage blower or the like. It will be appreciated that any such unit capable of moving large masses of air and which is driven by motor 22 will be suitable. Thus as can be seen, air moving unit or fan 28 is located within an air passage chamber 30 such that a large volume of air is moved from input port 12 through chamber 30 and out exhaust 14. Also as is shown, heating element 24 is located in air passage 30 such that when energized, the volume of air passing through chamber 30 is heated. Also as is shown, and for purposes of protection and preventing tampering or vadalism there is a grill 32 over intake port 12 to prevent the introduction of foreign items into air passage 30. Thus, as will be appreciated, the unit operates by pushing the activation button 16 which activates the blower 28 and the heating element 24 such that a large mass of warm hot air is provided out of exhaust port 14 for purposes of drying the operator's hand or face. After a selected period of time, timer 18 deactivates the blower and heating element and the unit is automatically turned off.

Referring now to FIG. 2, there is shown a diagrammatic illustration of the hot air hand dryer of FIG. 1 as described, but which includes one embodiment of this present invention. As shown in FIG. 2, the hot air hand dryer of FIG. 1 is mounted to a wall surface 34 by any suitable means such as wall bolts 36 and 38. Therefore, as is shown, a container means 40 having plurality of perforations such as shown at 42 is attached by any suitable means known to those skilled in the art to the air blower at the intake port 12 such that cold air indicated by arrows 44A and 46A must pass through container means 40 as shown by arrows 44B and 46B. The air enters air chamber 30, is moved pass heating element 24 and out the exhaust port 14 as hot air as is indicated by arrows 44C and 46C. Therefore, as is shown, container 40 includes a recharging slot 48 which is suitable for inserting a cake or stick of vaporizable deodorizer therethrough. The vaporizable deodorant 50 may be any suitable gel type product which has a low vapor pressure such that it vaporizes with the passage of air. Thus, it will be appreciated that in the operation of the hot air hand dryer which operates in conjunction with this invention, when the unit is activated by switch 16, cold air flow indicated by arrows 44A and 46A are drawn into ports 42 past deodorizing source or block 50 and enter chamber 30 of the hot air blower through grating 32 as cool deodorized air, and as indicated by arrows 44B and 46B. This cool deodorized air is then heated by element 24 and exhausted as hot deodorized air through exhaust port 14 as indicated by arrows 44C and 46C. In the embodiment shown in FIG. 2, the container 40 is shown with oversized edges 52 and 54 between the aperture 12 and the grating 32 such that permanent insulation is achieved. However, it will be appreciated that any means suitable for attaching container 40 to the hot air dryer will be satisfactory. For example, as shown in FIG. 3, the unit could simply be bolted to the hot air hand dryer, by bolts such as bolt 56. With such a unit, there would still be a slot 48 for inserting the cake or stick of deodorant. As seen, the slot 48 in container 40 of FIG. 2 would be suitable for accepting a deodorant stick such as shown in FIG. 4A, or a cake deodorant such as shown in 4B. Likewise, the container provided in FIG. 3 could accept either of these common shaped deodorized sources. It will be appreciated that it is not uncommon for a great deal of vandalism to occur in public washrooms or restrooms. Therefore, referring to FIG. 5 there is shown a container 40 which has a serpentine opening 58 which replaces the straight opening 48 as described hereinabove. Use of a serpentine opening 58 of course requires that only small pieces of a stick or cake such as shown in FIGS. 4A and 4B of deodorizing material be used or otherwise it is necessary that a serpentine cake or stick of deodorizer be used which will fit the opening 58. Thus, as shown in FIG. 6 there is shown a serpentine shaped cake of deodorizing material suitable for dropping into container 40 through slot 58. The use of such odd shaped sources prevents the introduction of sticks and other foreign matter into the container 40. Also as shown in FIG. 5, container 40 may be snapped into place onto hot air hand dryer of FIG. 2 by means of a snap in spring snaps on ears 60 and 62 as shown.

Referring to FIG. 7, there is shown still another means for attaching container 40 to the bottom portion of the hot air hand dryer. According to this embodiment, there is shown a piano hinge 64 which would be mounted to the bottom edge 66 of hot air hand dryer shown in FIG. 2 such that a single screw such as shown at 68 could be mounted through the lip 70 defining aperture 72. As shown, in FIG. 7, a simple screw would be loosened, the container swung down and the cake or source of deodorant material placed therein and then the container again secured to the hot air hand dryer.

It will also, of course, be appreciated that direct attachment to the container 40 to the hot air hand dryer is not in itself necessary for achieving the purposes of this invention. For example, as shown in FIG. 8 it may be desirable to simply attach the container 40 to wall 34 in close proximity to the intake port 12 of the hot air hand dryer such that the air flow through the intake port was drawn past container 40 in any deodorizing source contained therein.

In addition, it should be appreciated that although any standard commercially available product such as the commercially available gel type products would be suitable for use with this invention, it would be appreciated that because of the large amount of air volume drawn past the deodorizing source, a deodorizing source or cake of material having a lower vapor pressure could be used and still obtain satisfactory results. With the use of such a high vapor pressure source, the deodorizer would not be exhausted during nonuse periods of the restroom.

In addition, as shown in FIG. 9 it would also be in accordance with the teachings of this invention to include a container 72 downstream of the hot air heating element 74 such that hot air is drawn past the deodorant source 76 contained in container 72. In such an instance, it would be appreciated that a deodorizing source having a vaporizing temperature significantly higher than normal would be necessary. For such a design, it will be appreciated that the deodorizing source would be even less likely to vaporize during nonuse periods, since the normal room temperature would never achieve the level of the hot air used by the hand dryer. Of particular importance is the fact that this invention does provide a very simple, effective and efficient technique for dispensing deodorant vapors. Further, since the use of the hot air hand dryer itself will be in direct proportion to the use of the restroom or washroom, this means that in turn that the amount of deodorant used is also in direct proportion to the amount of useage of the restroom and washroom. Thus, there will be no waste or use of deodorant when the restroom is not used. Yet, at the same time there will be substantial use of the deodorant during substantial use of the restroom.

Thus, although the present invention has been described with respect to specific embodiments of apparatus for providing controlled deodorizing of a selected room, it is not intended that such specific references be considered as limitations upon the scope of this invention except insofar as is set forth in the following claims.

What is claimed is:

1. A combination room deodorizer and hot air hand dryer comprising:
    a housing dedicated to containing said hot air hand dryer, and defining an air intake port and an air exhaust port;
    electrical means permanently secured and located in said housing for heating air flowing therethrough;
    air moving means permanently secured in said housing for drawing air into said housing through said intake port, past said means for heating, and exhausting heated air from said housing through said exhaust port for drying hands;
    electrical driving means permanently secured in said housing for driving said air moving means;
    electrical switching means operable from outside said housing for providing electrical energy to said electrical driving means;
    container means detachably secured outside of said housing and juxtaposed said intake port of said housing, said container means defining an opening having selected cross-sectional dimensions so as to prevent the insertion of foreign objects; and
    a vaporizable deodorizer having initial cross-sectional dimensions substantially the same as said selected cross-sectional dimensional of said opening and located in said container means such that air is drawn past said deodorizer prior to entering said intake port, and heated air containing vapor from said deodorizer is exhausted through said exhaust port for drying hands and deodorizing the surrounding environment.

2. The apparatus of claim 1 wherein said selected shape is serpentine shape.

* * * * *